(12) United States Patent
Kilemnick et al.

(10) Patent No.: US 8,603,187 B2
(45) Date of Patent: Dec. 10, 2013

(54) DEVICE FOR DILATING THE URETHRA OF THE BODY OF A PATIENT AND DEVICE FOR REMOVING PROSTATE TISSUE

(75) Inventors: Ido Kilemnick, Hertzelia (IL); Oded Loebl, Kiriat Gat (IL)

(73) Assignee: Medi-Tate, Kiriat Gat (IL)

( * ) Notice: Subject to any disclaimer, the term of this patent is extended or adjusted under 35 U.S.C. 154(b) by 405 days.

(21) Appl. No.: 12/598,996

(22) PCT Filed: May 7, 2008

(86) PCT No.: PCT/IL2008/000639
§ 371 (c)(1),
(2), (4) Date: Feb. 3, 2010

(87) PCT Pub. No.: WO2008/136005
PCT Pub. Date: Nov. 13, 2008

(65) Prior Publication Data
US 2010/0137893 A1 Jun. 3, 2010

Related U.S. Application Data

(60) Provisional application No. 60/916,460, filed on May 7, 2007.

(51) Int. Cl.
*A61F 2/04* (2013.01)
*A61B 17/122* (2006.01)

(52) U.S. Cl.
USPC ...................................... 623/23.66; 606/157

(58) Field of Classification Search
USPC ......... 606/110, 113, 170, 180, 190, 191, 198, 606/200, 151, 157; 623/23.66; 600/562, 600/570
See application file for complete search history.

(56) References Cited

U.S. PATENT DOCUMENTS

| 5,643,304 A | 7/1997 | Schechter et al. |
| 2002/0010487 A1* | 1/2002 | Evans et al. ................. 606/180 |

FOREIGN PATENT DOCUMENTS

| WO | WO99/60935 | 12/1999 |
| WO | WO03/022157 | 3/2003 |
| WO | WO2006/040767 | 4/2006 |

OTHER PUBLICATIONS

International Preliminary Report on Patentability for PCT/IL2008/000639 (Nov. 10, 2009).
International Search Report for PCT/IL2008/000639 (Oct. 29, 2008).
Written Opinion for PCT/ PCT/IL2008/000639 (Oct. 29, 2008).

* cited by examiner

*Primary Examiner* — Kathleen Holwerda
*Assistant Examiner* — Sarah W Aleman
(74) *Attorney, Agent, or Firm* — Choate, Hall & Stewart LLP; Fangli Chen; Daniel S. Matthews

(57) ABSTRACT

Device for removing prostate tissue from within the urethra, the device including a plurality of arms, and an actuating mechanism coupled to the arms, the arms being rotatable about a longitudinal axis of the urethra, the arms being divided into arm pairs, each of the arm pair being apart from each other in a first configuration and attempting to get closer to each other, in a second configuration, wherein the device is inserted in the urethra toward the prostate, in the first configuration, and wherein after the device is placed adjacent to the prostate, within the urethra, the actuating mechanism moves the arms to the second configuration, thereby pinching the prostate through the urethra.

3 Claims, 24 Drawing Sheets

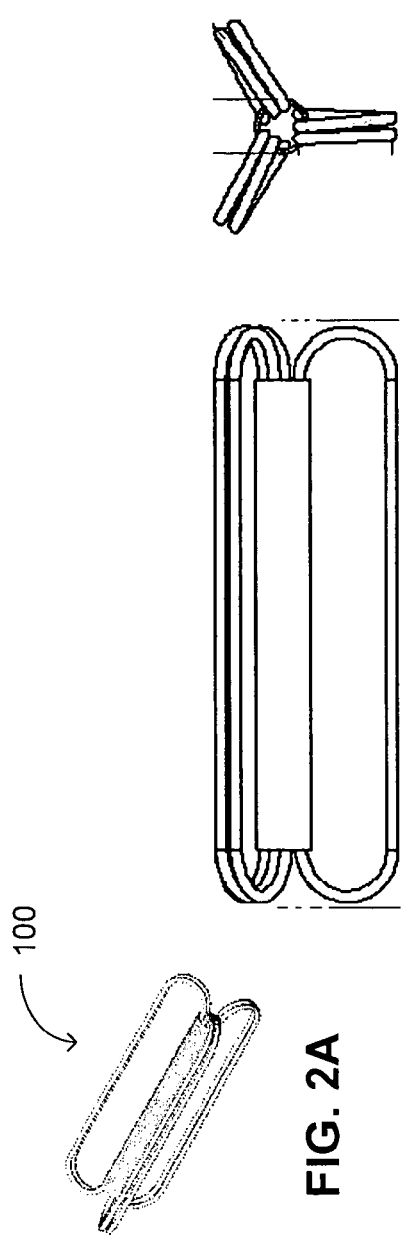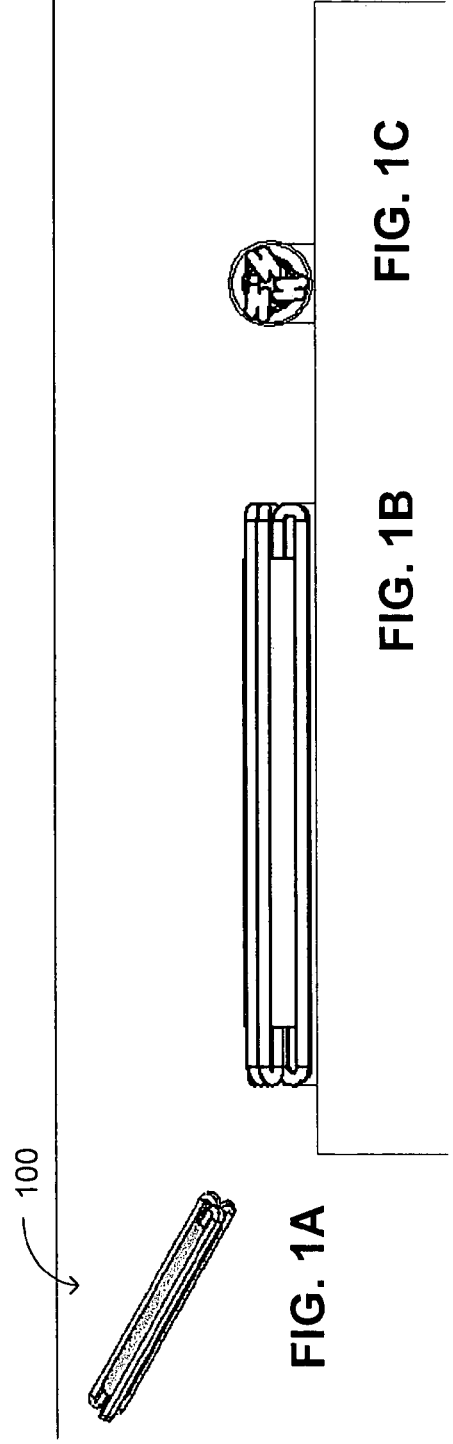

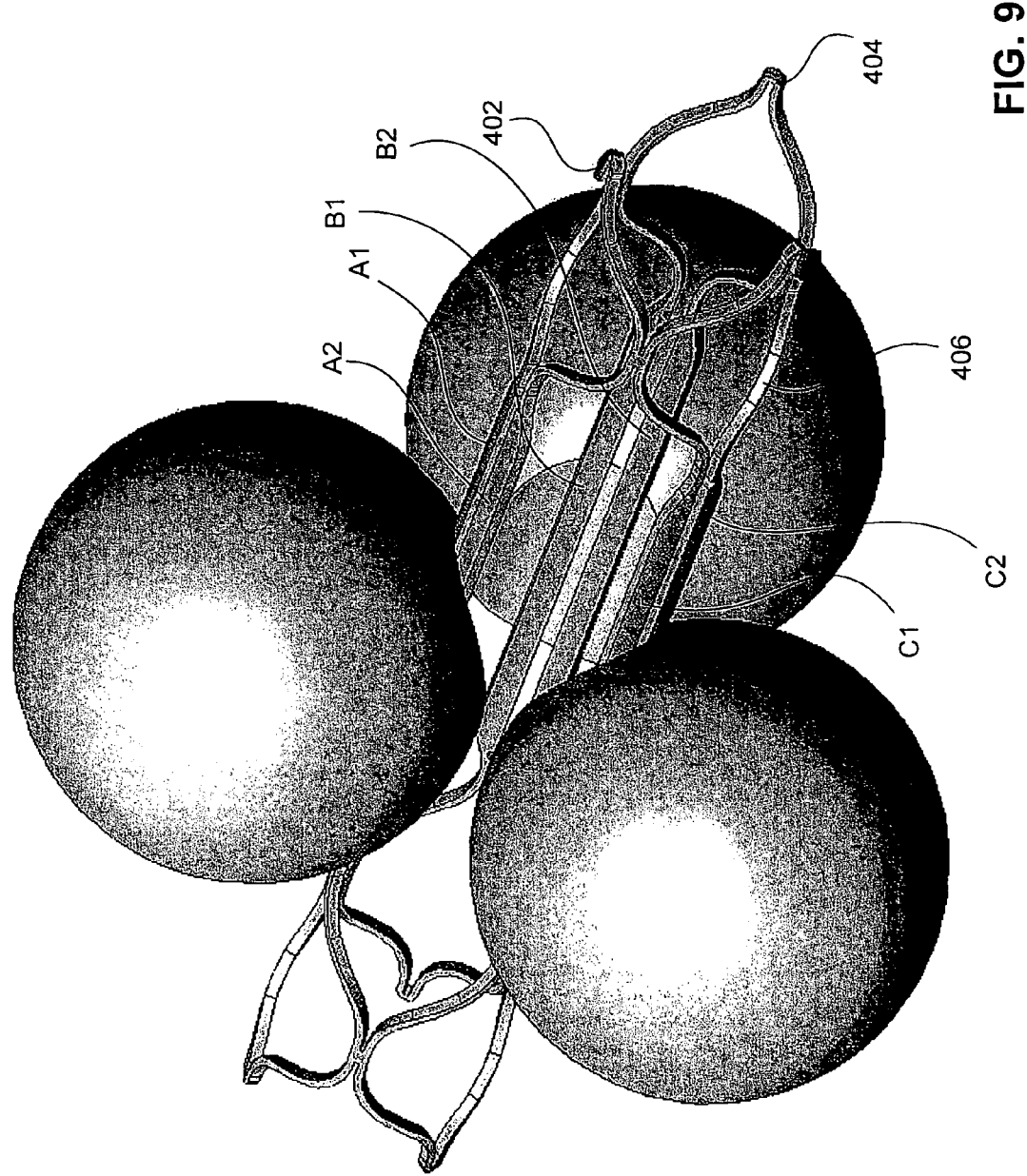

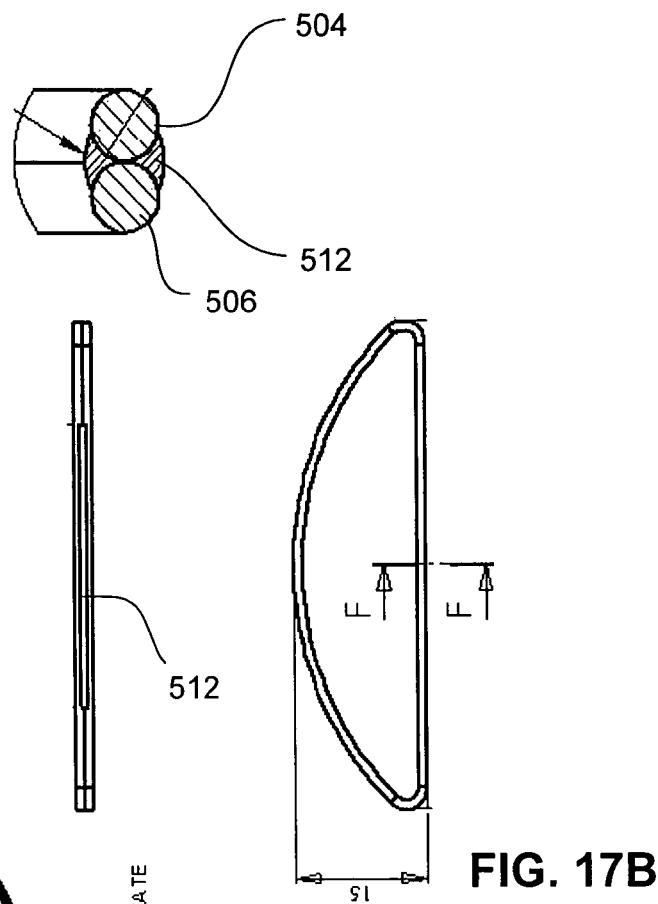

DEVICE FOR DILATING THE URETHRA OF THE BODY OF A PATIENT AND DEVICE FOR REMOVING PROSTATE TISSUE

CROSS REFERENCE TO RELATED APPLICATIONS

This Application claims the benefit under 35 U.S.C. §371 of International Application No.: PCT/IL2008/000639, filed May 7, 2008 (published PCT application No. WO 2008/136005 A1, on Nov. 13, 2008), which claims priority to U.S. provisional application, Ser. No. 60/916,460, filed May 7, 2007, the entire contents of each of which are incorporated herein by reference.

FIELD OF THE DISCLOSED TECHNIQUE

The disclosed technique relates to medical devices in general, and to methods and systems for treating prostatitis, in particular.

BACKGROUND OF THE DISCLOSED TECHNIQUE

Prostate enlargement is prevalent among the elderly, causing a number of complications, such as urinary frequency and urgency at night, burning or painful urination, body aches, and infection of the urinary tract. The prostate gland which surrounds a portion of the urethra (i.e., the lumen which connects the urinary bladder to outside of the body), is swelling enlarged over time (i.e., BPH—benign prostate hyperplasia), compressing the urethra, and restricting urinary flow.

Devices and methods for treating prostate enlargement are known in the art. One such method involves a surgical procedure (i.e., prostatectomy, TURP—Transurethral resection of the prostate) in which the enlarged portions of the prostate gland are incised. Another method involves the insertion of an elongated instrument called resectoscope, which is inserted into the penis, and includes an electrical loop for removing the obstructing tissue and sealing the blood vessels. International Publication Number WO 2006/0404767 A1 to Sivan et al., and entitled "Prostate Treatment Stent", is directed to a device for removing the urethra and prostate tissue, in a non-invasive manner. The device is in form of a coil, which is either made of a shape memory alloy, or an elastic material. The coil is inserted into the urethra in an expanded form, and later retracted along a longitudinal axis thereof. The axial retraction causes the coil to pinch the tissue of the urethra and the prostate over time, thereby restricting blood flow to the tissue. The lack of blood flow to the tissue causes the tissue to dry out and dislodge from the rest of the prostate gland, and carried out of the urethra by the urine stream.

SUMMARY OF THE DISCLOSED TECHNIQUE

It is an object of the disclosed technique to provide a novel method and system for removing portions the tissue of an enlarged prostate of the body of a patient which overcomes the disadvantages of the prior art.

According to the disclosed technique, there is thus provided a device for removing prostate tissue from within the urethra. The device includes a plurality of arms, and an actuating mechanism coupled to the arms. The arms are rotatable about a longitudinal axis of the urethra. The arms are divided into arm pairs. Each of the arm pair is apart from each other in a first configuration and attempt to get closer to each other, in a second configuration. The device is inserted in the urethra toward the prostate, in the first configuration, and after the device is placed adjacent to the prostate, within the urethra, the actuating mechanism moves the arms to the second configuration, thereby pinching the prostate through the urethra.

According to another aspect of the disclosed technique, there is thus provided a device for removing a tissue portions of an enlarged prostate of the body of a patient. The device is inserted into the prostate, through an urogenital system of the body of the patient. The device includes a plurality of rotatable arms. The rotatable arms are in a first configuration, while the device is being inserted into the prostate. The rotatable arms of every second configuration adjacent arms pair of the rotatable arms, rotatably move from the first configuration toward a second configuration, over respective regions of the enlarged portion. One of the rotatable arms of a respective one of a first configuration adjacent arms pair, belongs to a respective one of the second configuration adjacent arms pair, another one of the rotatable arms of the respective first configuration adjacent arms pair, belongs to another one of the second configuration adjacent arms pair. The respective second configuration adjacent arms pair, is adjacent to the other second configuration adjacent arms pair.

The rotatable arm ends of rotatable arms of every one of the second configuration adjacent arms pair, are coupled together by a respective closed loop wire of a plurality of closed wire loops. Each of the closed loop wires is made of a shape memory alloy. Adjacent ones of the closed loop wires are coupled together at a pair of coupling points. Two extreme ones of the closed loop wires are coupled together at respective ones of the pair of coupling points, to form a closed loop assembly of rotatable arms. Rotatable arms of the first configuration adjacent arms pair, are close to one another, and rotatable arms of the second configuration adjacent arms pair, are away from one another, when each of the closed loop wires is at a first temperature, and when the rotatable arms are in the first configuration. Rotatable arms of the second configuration adjacent arms pair, rotatably move toward one another, about a longitudinal axis of the closed loop assembly of rotatable arms, when each of the closed loop wires is at a second temperature, and when the rotatable arms are in the second configuration.

BRIEF DESCRIPTION OF THE DRAWINGS

The disclosed technique will be understood and appreciated more fully from the following detailed description taken in conjunction with the drawings in which:

FIG. 1A is a schematic illustration of a device for dilating the urethra of the body of a patient, in perspective, constructed and operative in accordance with an embodiment of the disclosed technique, in a folded configuration;

FIG. 1B is a schematic illustration of a top view of the device of FIG. 1A;

FIG. 1C is a schematic illustration of a side view of the device of FIG. 1A;

FIG. 2A is a schematic illustration of a perspective view of the device of FIG. 1A, in an open configuration;

FIG. 2B is a schematic illustration of a top view of the device of FIG. 2A;

FIG. 2C is a schematic illustration of a side view of the device of FIG. 2A;

FIG. 6B is a schematic illustration of a side view of the device of FIG. 6A, in a further advanced stage;

FIG. 9 is a schematic illustration in perspective, of the device of FIG. 8, in an operational configuration, within the urethra;

FIG. 15A is a schematic illustration in perspective, of the device of FIG. 12, in the open configuration;

FIG. 15B is a schematic illustration in perspective, of the device of FIG. 12, in the closed configuration;

FIG. 16A is a schematic illustration of a side view of the device of FIG. 15A;

FIG. 16B is a schematic illustration of a side view of the device of FIG. 15B;

FIG. 17A is a schematic illustration of a side view of the device of FIG. 15B;

FIG. 17B is a schematic illustration of a top view of the device of FIG. 15B;

FIG. 17C is a schematic illustration of a cross section of the device of FIG. 17B.

DETAILED DESCRIPTION OF THE EMBODIMENTS

The disclosed technique overcomes the disadvantages of the prior art by providing a device having a plurality of arms which can rotate about a longitudinal axis. After placing the device in a desired location within the urethra of the body of a patient, the arms are released from a folded configuration to an open configuration. An elastic force causes the arms to rotate about the longitudinal axis, wherein each pair of the arms pinches the local tissue of the urethra and the prostate, eventually stopping blood flow to that region, and dislodging a portion of the tissue from the urethra and the prostate. When the arms fully close in on the tissue (i.e., pinched), necrosis begins, which may take between three to twenty eight one days, the device is removed from the body of the patient. The dead, and in some cases also shrunk, dry tissue is carried out of the urethra by the urinary stream, or by a removal tool.

Figure 3:
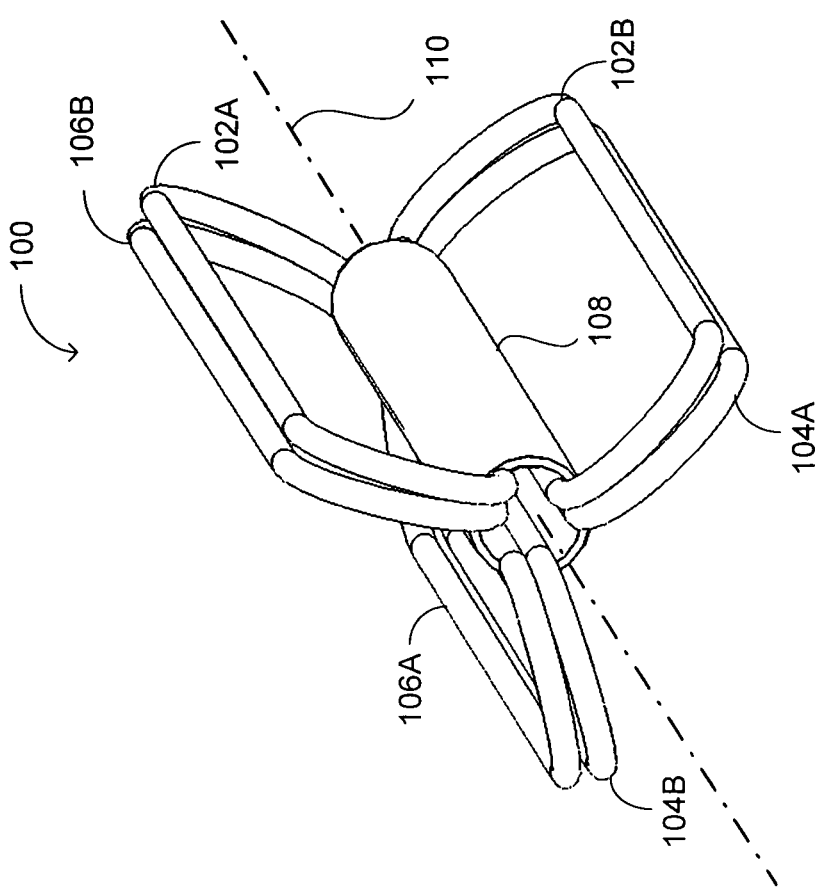
FIG. 3 is a schematic illustration of a perspective view of the device of FIG. 2A in an open configuration.
Figure 4A:
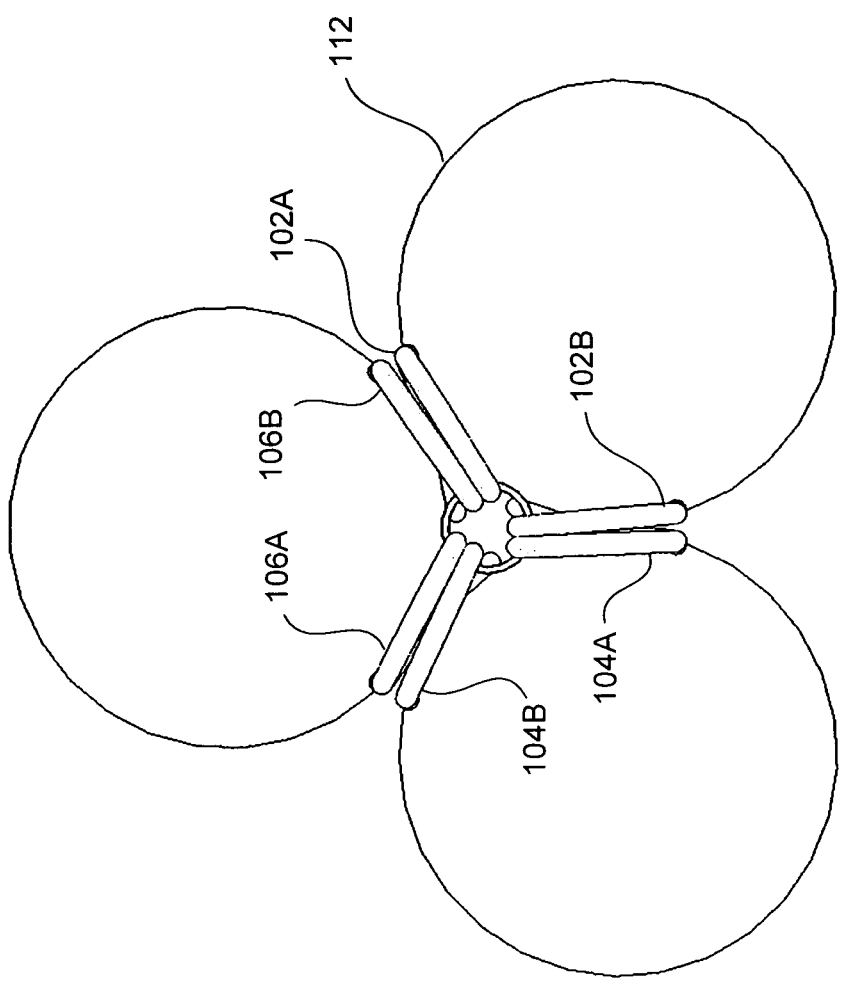
FIG. 4A is a schematic illustration of the device of FIG. 3, placed within the urethra, in an open configuration.
Figure 4B:
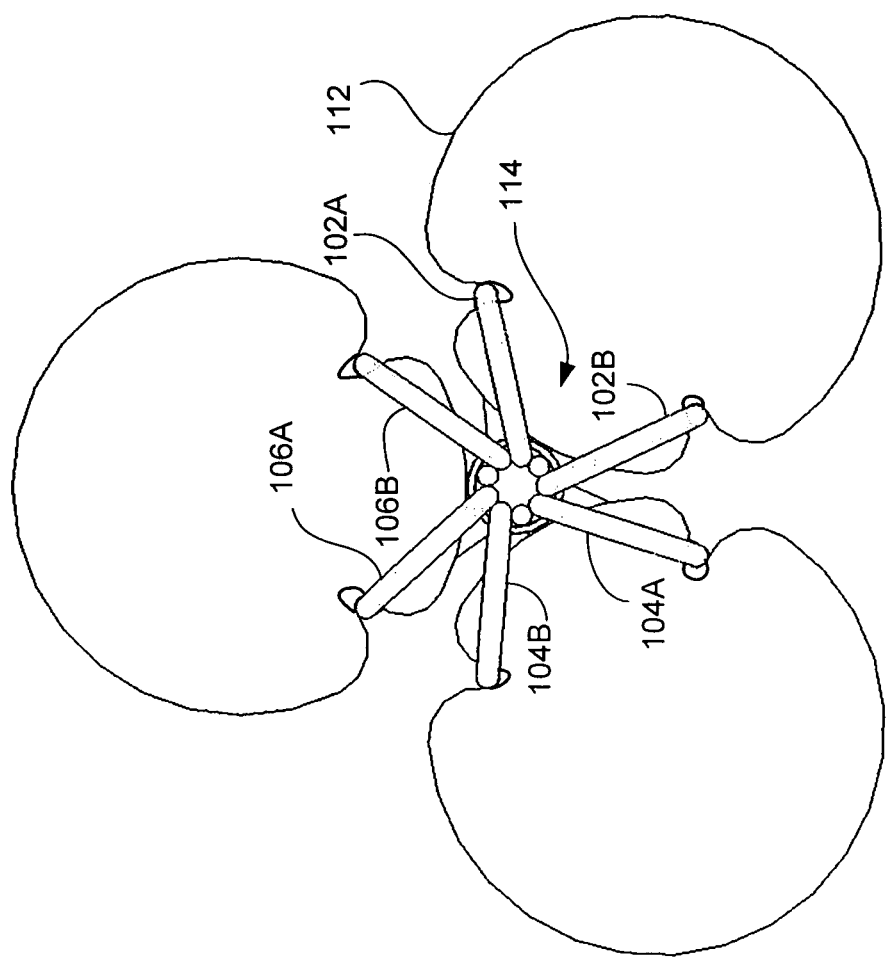
FIG. 4B is a schematic illustration of the device of FIG. 3, wherein each pair of the arms of the device begin to pinch the respective region of the urethra and the prostate.
Figure 4C:
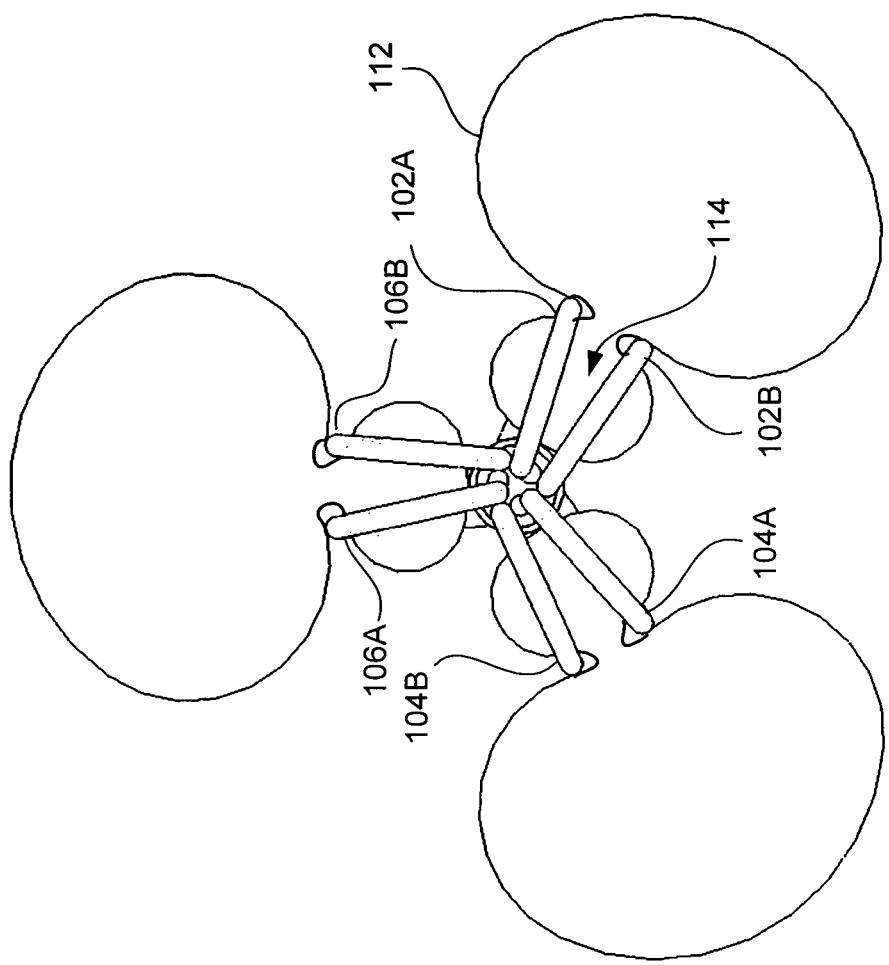
FIG. 4C is a schematic illustration of the device of FIG. 3, wherein each pair of the arms of the device approach one another further, thereby further pinching the respective region of the urethra, and beginning to isolate that region of the tissue from the surrounding.
Figure 4D:
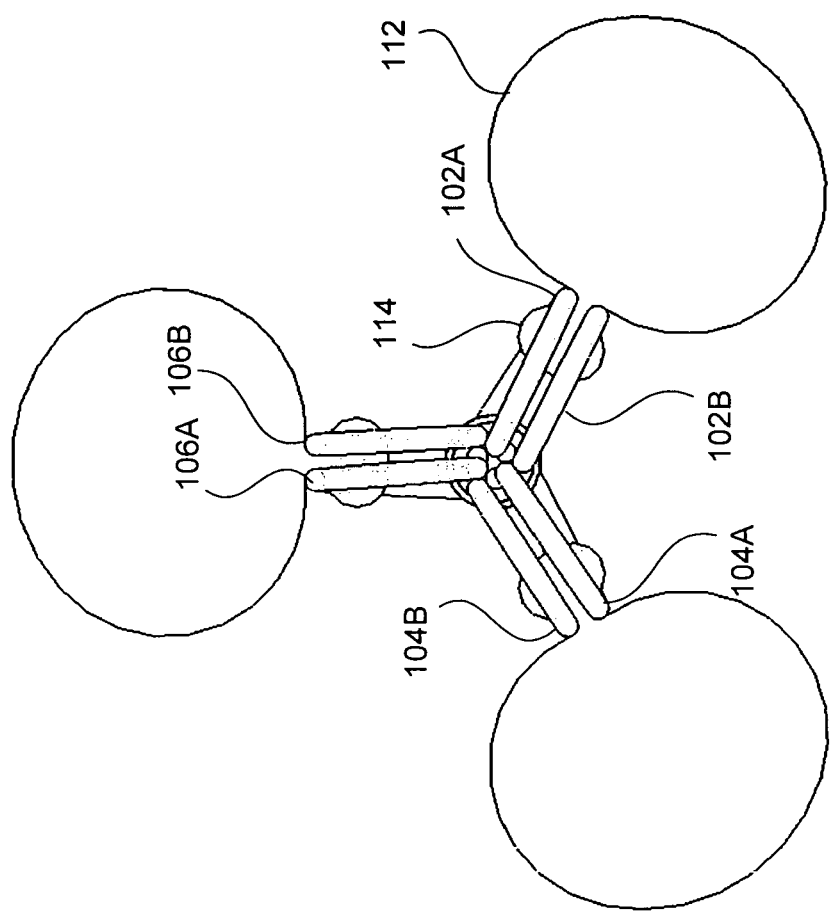
FIG. 4D is a schematic illustration of the device of FIG. 3, with each pair of the arms further approaching one another.
Figure 4E:
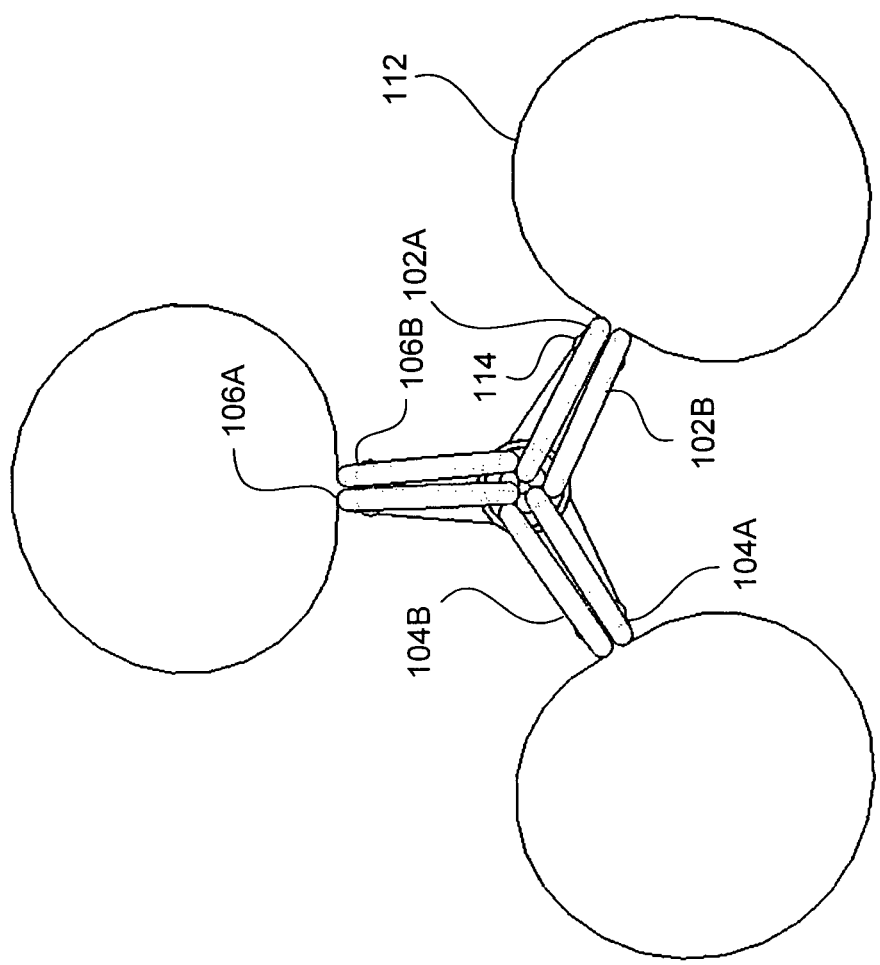
FIG. 4E is a schematic illustration of the device of FIG. 3, wherein each pair of the arms have made contact with one another, and the respective regions of the urethra and the prostate are substantially isolated from the rest.

Reference is now made to FIGS. 1A, 1B, 1C, 2A, 2B, 2C, 3, 4A, 4B, 4C, 4D, and 4E. FIG. 1A is a schematic illustration of a device for removing prostate issue from the body of a patient, in perspective, generally referenced 100, constructed and operative in accordance with an embodiment of the disclosed technique, in a folded configuration. FIG. 1B is a schematic illustration of a top view of the device of FIG. 1A. FIG. 1C is a schematic illustration of a side view of the device of FIG. 1A. FIG. 2A is a schematic illustration of a perspective view of the device of FIG. 1A, in an open configuration. FIG. 2B is a schematic illustration of a top view of the device of FIG. 2A. FIG. 2C is a schematic illustration of a side view of the device of FIG. 2A. FIG. 3 is a schematic illustration of a perspective view of the device of FIG. 2A in an open configuration. FIG. 4A is a schematic illustration of the device of FIG. 3, placed within the urethra, in an open configuration. FIG. 4B is a schematic illustration of the device of FIG. 3, wherein each pair of the arms of the device begin to pinch the respective region of the urethra and the prostate. FIG. 4C is a schematic illustration of the device of FIG. 3, wherein each pair of the arms of the device approach one another further, thereby further pinching the respective region of the urethra, and beginning to isolate that region of the tissue from the surrounding. FIG. 4D is a schematic illustration of the device of FIG. 3, with each pair of the arms further approaching one another. FIG. 4E is a schematic illustration of the device of FIG. 3, wherein each pair of the arms have made contact with one another, and the respective regions of the urethra and the prostate are substantially isolated from the rest.

With reference to FIG. 3, device 100 includes a plurality of arms (i.e., rotatable arms) 102A, 102B, 104A, 104B, 106A, and 106B, a central tube 108 (which is a part of an actuating mechanism—not shown), and a catheter (not shown). The actuating mechanism can be in the form of an actuator known in the art, such as rotary electric motor, linear electrical motor, pneumatic motor, hydraulic motor, piezoelectrical element, electromagnetic element, mechanical energy converter (e.g., a spring), pressurized fluid accumulator (such as compressed gas bladder), mechanical and manually operated, and the like. In case the actuating mechanism is made of an elastic material, the energy level of the actuating mechanism drops, when the rotatable arms move from the folded configuration, toward the open configuration. Each of arms 102A, 102B, 104A, 104B, 106A, and 106B, is in form of a non-cutting device, having a blunt edge. Each of the arms 102A, 102B, 104A, 104B, 106A, and 106B, is rotatably coupled with central tube 108, such that it can rotate about a longitudinal axis 110 of central tube 108. The coupling between arms 102A, 102B, 104A, 104B, 106A, and 106B, and central tube 108 is an elastic coupling, so that each of arms 102A, 102B, 104A, 104B, 106A, and 106B, rotates in a direction about longitudinal axis 110, which causes the respective pair of the arms to approach one another. Device 100 is made of a biocompatible material such as Titanium, and the like, or a shape memory alloy, such as Nitinol, and the like. For example, the shape memory alloy is in a martensite state when the arms are in the folded configuration, and in an austenite state, when the arms are in the open configuration. The elastic force can act for example, due to one or more springs, shape memory effect, and the like.

Following is a description of a medical operation on the urogenital system of the body of a patient, by employing device 100. An over-tube (not shown) is inserted into the urethra (not shown) of the body of a patient (not shown), while a physician (not shown) visually observes the advancement of the over-tube for example, by employing a cystoscope (not shown). Once the physician ensures that the over-tube has reached the desired location within the urethra, the physician inserts an implant-holder (i.e., a catheter—not shown), within the over-tube. Arms 102A, 102B, 104A, 104B, 106A, and 106B, are attached to a distal portion of the implant-holder, and are kept in a folded configuration, by being constricted inside the over-tube (FIG. 1A). Once the physician ensures that arms 102A, 102B, 104A, 104B, 106A, and 106B, are located at the desired location within the urethra, the physician pulls out the over-tube, thereby causing arms 102A, 102B, 104A, 104B, 106A, and 106B, to deploy to an open configuration, by rotating about the longitudinal axis of central tube 108, due to an elastic force between arms 102A, 102B, 104A, 104B, 106A, and 106B, and central tube 108 (FIG. 2A).

With reference to FIG. 4A, each pair of arms 102A, 102B, 104A, 104B, 106A, and 106B, begins to make contact with the respective region of the urethra and the prostate. For example, arms 102A and 102B make contact with a region 112 of the prostate. With reference to FIG. 4B, in an advanced stage, arms 102A and 102B begin to constrict a portion 114 of region 112, by approaching one another, and thereby pinching the tissue of region 112. This constriction of portion 114 restricts the blood flow to portion 114, and induces ischemia in portion 114. With reference to FIG. 4C, with further approach of arms 102A and 102B toward one another, portion 114 is further constricted, thereby further restricting the blood flow. With reference to FIG. 4D, arms 102A and 102B further approach one another, and portion 114 is further constricted thereby further restricting the blood flow.

With reference to FIG. 4E, device 100 advances to a final stage, wherein each pair of arms 102A, 102B, 104A, 104B, 106A, and 106B, make contact with one another, and substantially isolate the respective portion of the prostate, thereby substantially completely halting the blood flow to the respective portion. Lack of blood flow to this portion of the tissue, deprives the cells of vital nutrients, thereby eventually drying that portion of the tissue (i.e., necrosis). In a gradual process which might last between three to twenty eight days, the blood flow to portion 114 is progressively restricted, thereby isolating portion 114 from the rest of region 112 and depriving it of vital nutrients, and finally killing the cells of portion 114. These dead cells are carried by the urine stream of the patient, and eventually expelled from the urethra.

At this stage, the physician removes device 100 from the urethra, by employing a removal system (not shown). It is noted that during the entire treatment process as described in connection with FIGS. 4A, 4B, 4C, 4D, and 4E, central tube 108 maintains the urethra in an open condition, thereby facilitating normal flow of urine from the bladder (not shown) of the body of the patient, through the urethra. Removal of tissue from the inner wall of urethra and the prostate, dilates the urethra, which is previously constricted for example, due to prostatitis, benign prostate hyperplasia, and the like. It is further noted that the gradual pinching action brought about by device 100, involves minimal pain and discomfort on the part of the patient. Additionally, device 100 can be coated with a drug which is gradually released to the surrounding tissues. This drug can be for example, one which is aimed at reducing enlargement, preventing infection, or pain and the like, and thereby aid the treatment process.

Figure 5A:
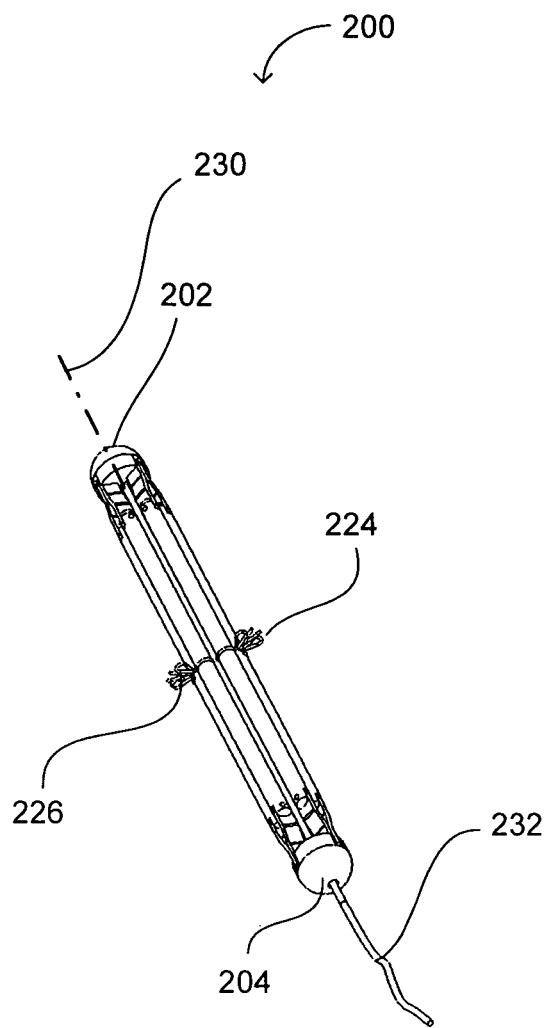
FIG. 5A is a schematic illustration in perspective, of a device for dilating the urethra of the body of a patient, constructed and operative in accordance with another embodiment of the disclosed technique, in a folded configuration.
Figure 5B:
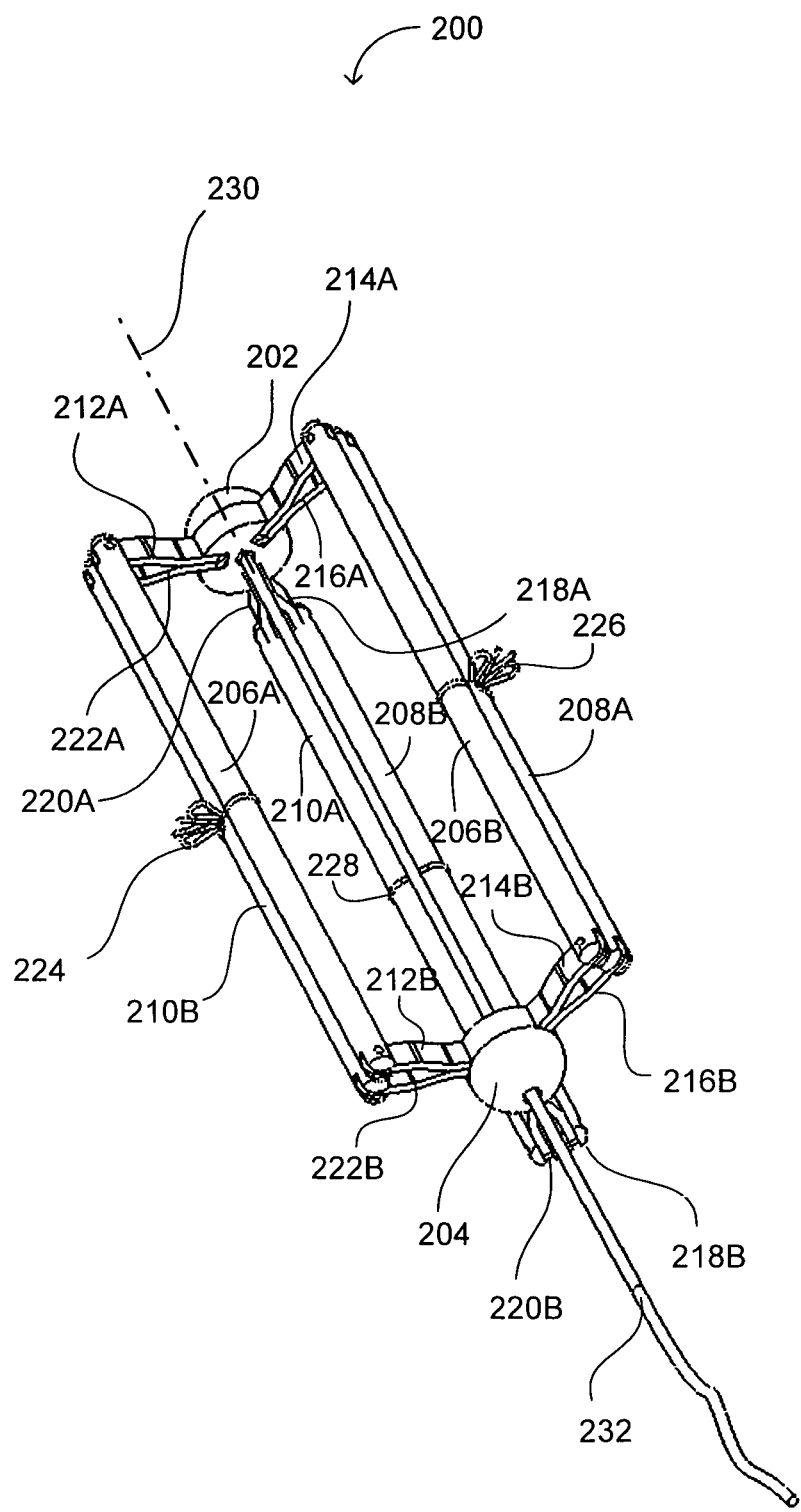
FIG. 5B is a schematic illustration in perspective, of the device of FIG. 5A, with the arms of the device in a deployed position, and each pair of arms still attached to one another.
Figure 5C:
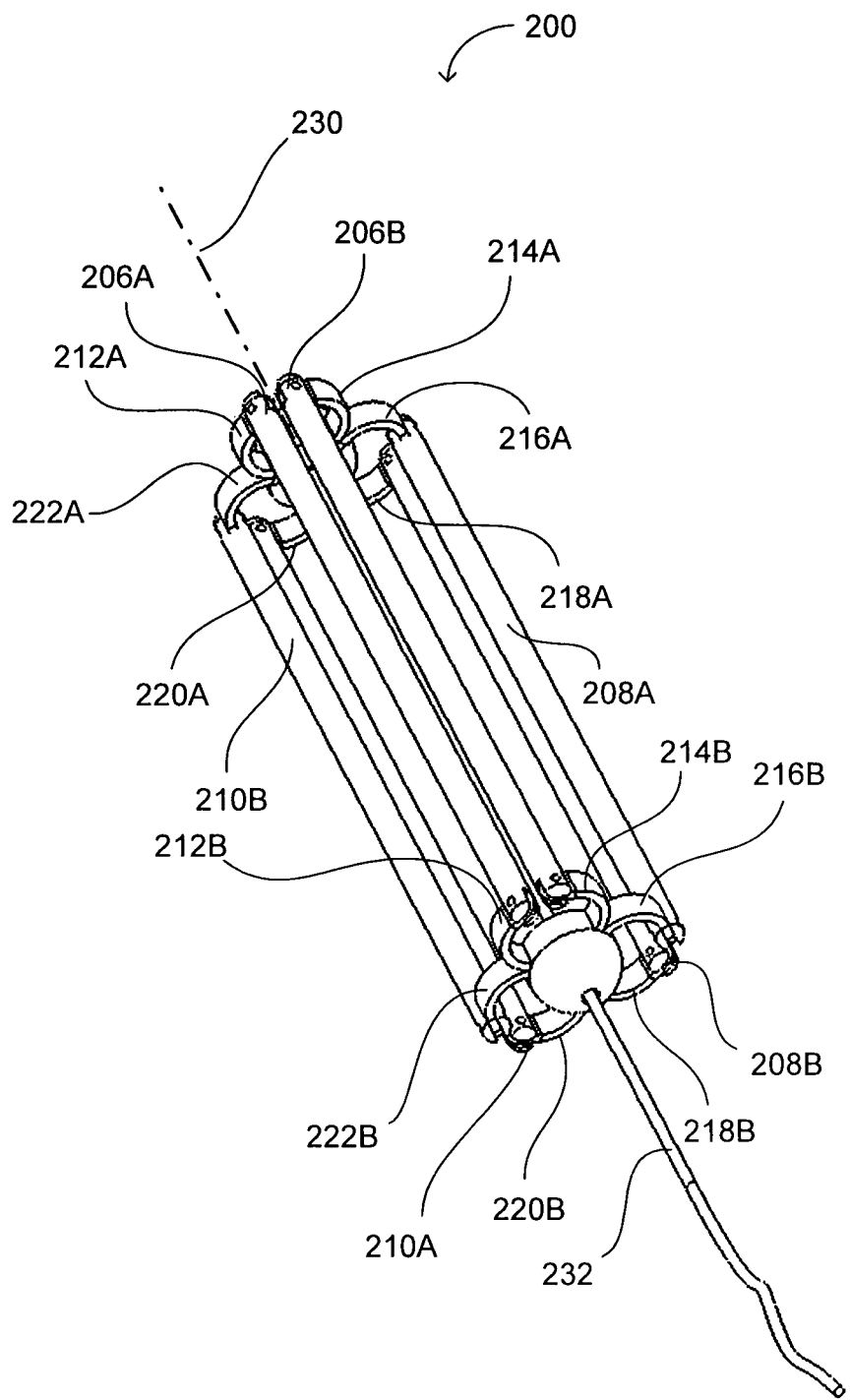
FIG. 5C is a schematic illustration in perspective, of the device of FIG. 5A, in which the respective arms of the device have approached one another.

Reference is now made to FIGS. 5A, 5B, and 5C. FIG. 5A is a schematic illustration in perspective, of a device for dilating the urethra of the body of a patient, generally referenced 200, constructed and operative in accordance with another embodiment of the disclosed technique, in a folded configuration. FIG. 5B is a schematic illustration in perspective, of the device of FIG. 5A, with the arms of the device in a deployed position, and each pair of arms still attached to one another. FIG. 5C is a schematic illustration in perspective, of the device of FIG. 5A, in which the respective arms of the device have approached one another.

Device 200 includes a front end 202, a rear end 204, a plurality of arms 206A, 206B, 208A, 208B, 210A, and 210B, and a plurality of elastic hinges 212A, 212B, 214A, 214B, 216A, 216B, 218A, 218B, 220A, 220B, 222A, and 222B. A front end of each of arms 206A, 206B, 208A, 208B, 210A, and 210B, is coupled with front end 202, by elastic hinges 212A, 214A, 216A, 218A, 220A, and 222A, respectively. A rear end of arms 206A, 206B, 208A, 208B, 210A, and 210B, is coupled with rear end 204, by elastic hinges 212B, 214B, 216B, 218B, 220B, and 222B, respectively.

With reference to FIG. 5B, arms 206A and 210B are tied together with a piece of string 224. Arms 206B and 208A are tied together with a piece of string 226. Arms 208B and 210A are tied together with a piece of string 228. In the folded configuration as illustrated in FIG. 5A, each of elastic hinges 212A, 212B, 214A, 214B, 216A, 216B, 218A, 218B, 220A, 220B, 222A, and 222B is positioned substantially parallel to a longitudinal axis 230 of device 200. One end of a string 232 is connected with front end 202, and the other end thereof is accessible by the physician from the outside of the urethra. The physician inserts device 200 into the urethra while device 200 is in the folded configuration as illustrated in FIG. 5A. Once the physician ensures that device 200 is located in the desired region of the urethra, the physician pulls an outer end of string 232, thereby moving front end 202 toward rear end 204. This action causes each of elastic hinges 212A, 212B, 214A, 214B, 216A, 216B, 218A, 218B, 220A, 220B, 222A, and 222B, to rotate relative to front end 202 and rear end 204, to a position substantially perpendicular to longitudinal axis 230, to the deployed configuration illustrated in FIG. 5B. In the configuration illustrated in FIG. 5B, arms 206A, 206B, 208A, 208B, 210A, and 210B, remain in a position substantially parallel to longitudinal axis 230, and still respectively tied together. By pulling string 232 the device moves from the configuration illustrated in FIG. 5A to the configuration illustrated in FIG. 5B (e.g., four bar mechanism).

With reference to FIG. 5C, the physician opens each of strings 224, 226, and 228. Alternatively, each of strings 224, 226, and 228 can be made of a biodegradable material, which is dissolved by the bodily fluids. The opening of each of strings 224, 226, and 228, causes the elastic forces of each of elastic hinges 212A, 212B, 214A, 214B, 216A, 216B, 218A, 218B, 220A, 220B, 222A, and 222B, to move the respective ones of arms 206A, 206B, 208A, 208B, 210A, and 210B, toward one another. In this manner, arm 206A moves toward arm 206B, arm 208A moves toward arm 208B, and arm 210A moves toward arm 210B, thereby pinching the respective portions of the tissue of the urethra and prostate.

Figure 6A:
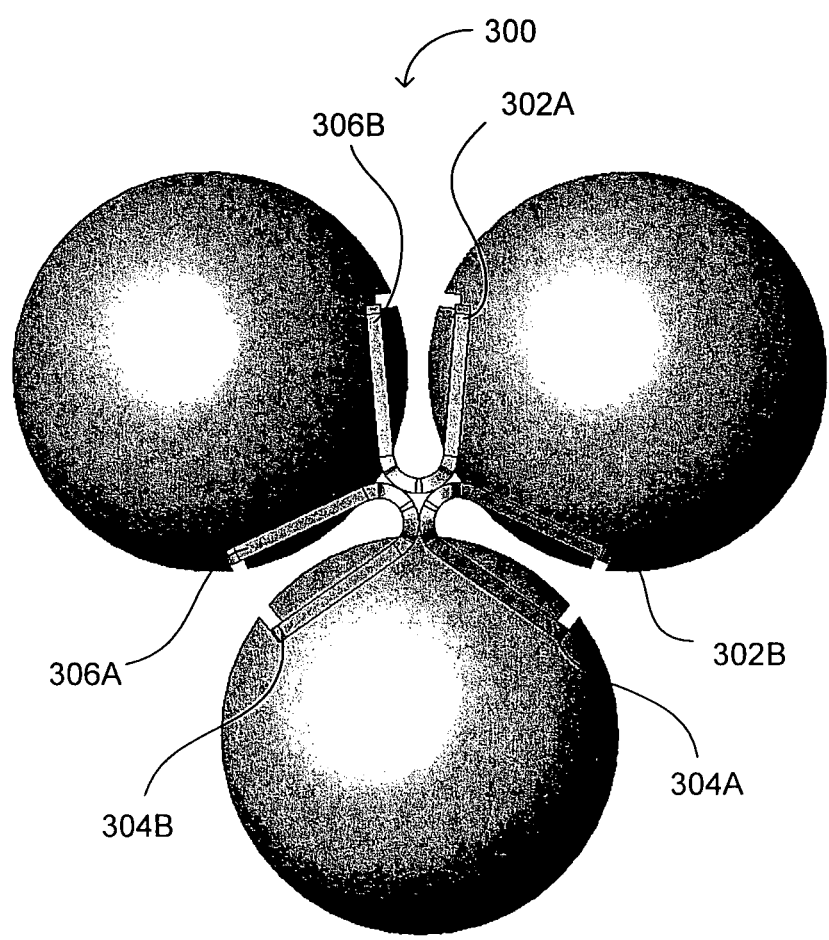
FIG. 6A is a schematic illustration of a side view of a device for removing tissue from the body of a patient, constructed and operative in accordance with a further embodiment of the disclosed technique, in an initial stage of operation.
Figure 6B:
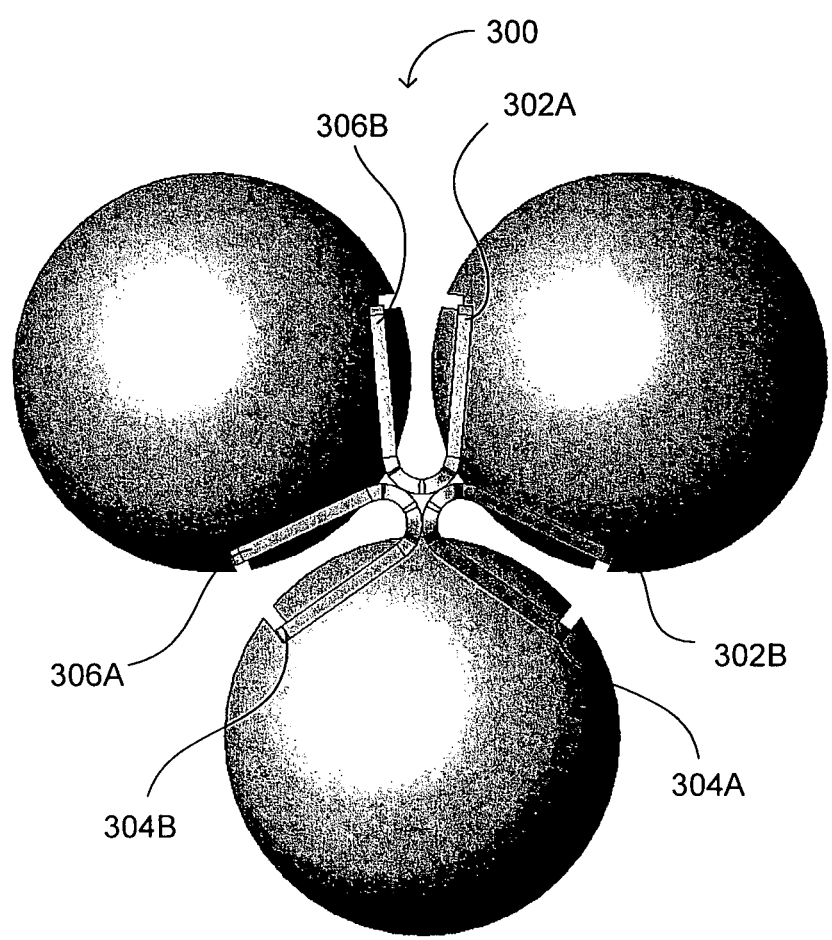
FIG. 6B, is a schematic illustration of a side view of the device of FIG. 6A, in an advanced stage.
Figure 6C:
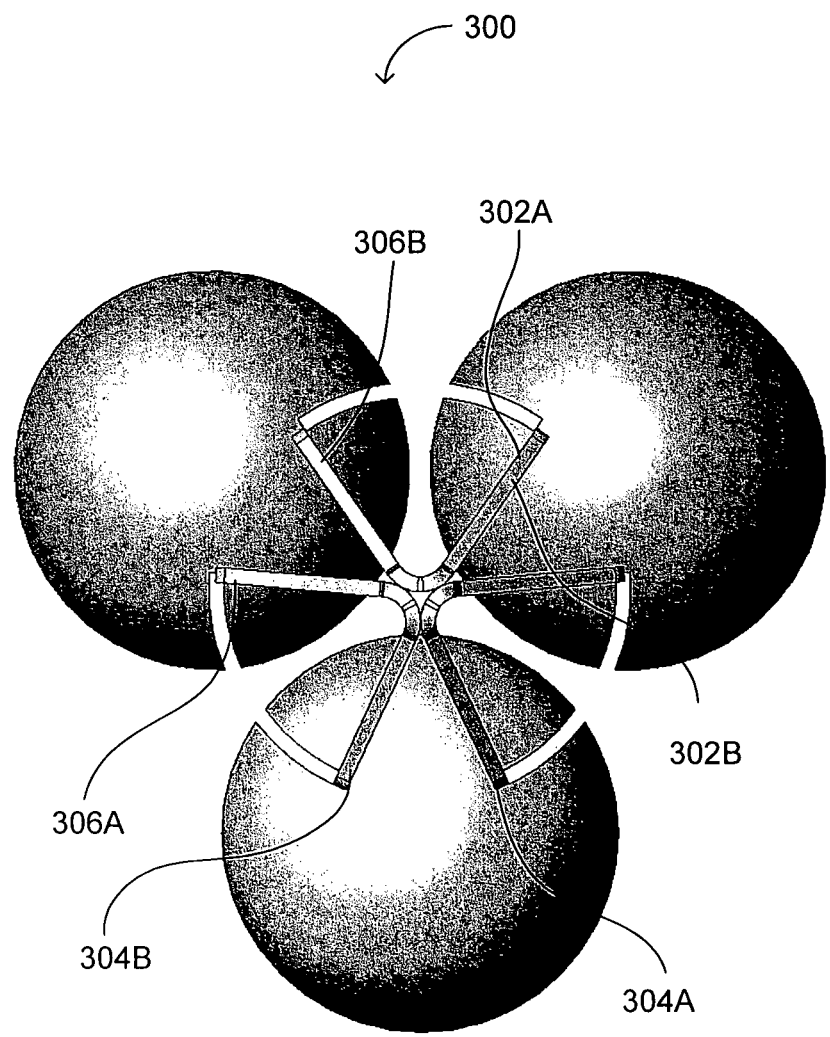
FIG. 6C is a schematic illustration of a side view of the device of FIG. 6A, in another advanced stage.
Figure 6D:
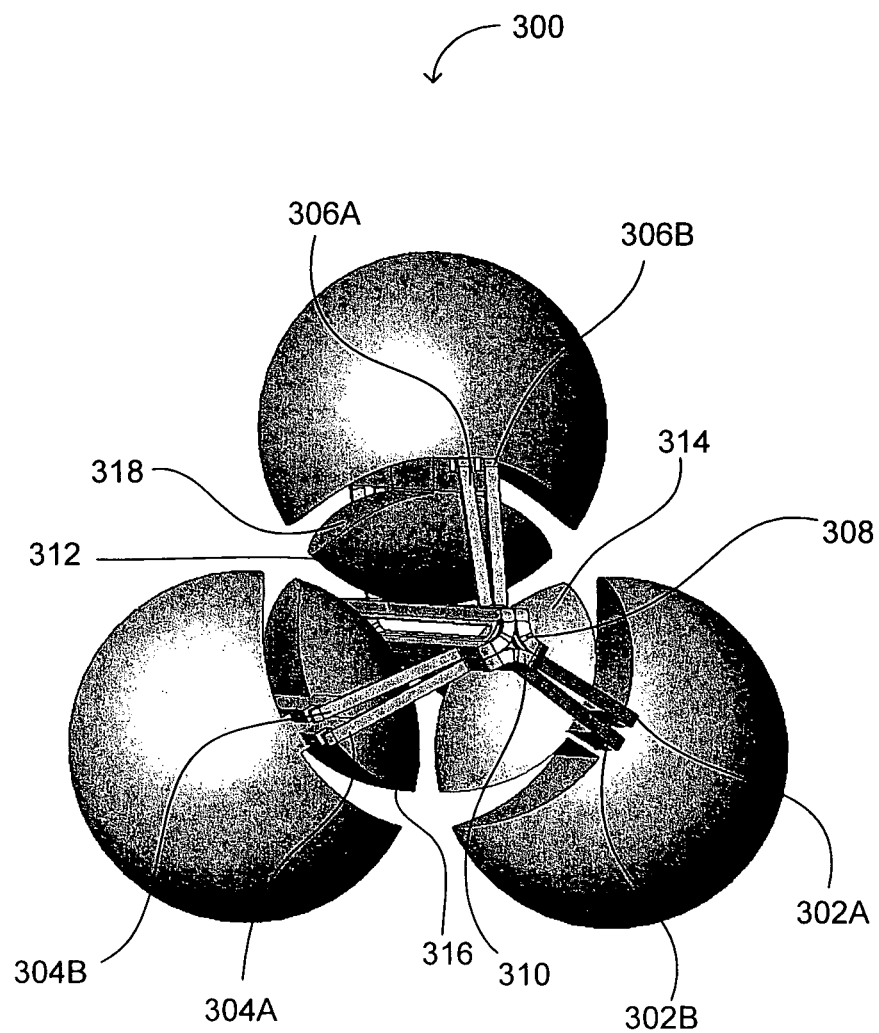
FIG. 6D is a schematic illustration of a perspective view of the device of FIG. 6A, in a final stage.

Reference is now made to FIGS. 6A, 6B, 6C, and 6D. FIG. 6A is a schematic illustration of a side view of a device for dilating a urethra of the body of a patient, generally referenced 300, constructed and operative in accordance with a further embodiment of the disclosed technique, in an initial stage of operation. FIG. 6B, is a schematic illustration of a side view of the device of FIG. 6A, in an advanced stage. FIG. 6B is a schematic illustration of a side view of the device of FIG. 6A, in a further advanced stage. FIG. 6C is a schematic illustration of a side view of the device of FIG. 6A, in another advanced stage. FIG. 6D is a schematic illustration of a perspective view of the device of FIG. 6A, in a final stage.

Device 300 includes arms 302A, 302B, 304A, 304B, 306A, and 306B. Each of arms 302A, 302B, 304A, 304B, 306A, and 306B includes a compression link (not shown), and a pair of legs (not shown). Each end of each compression link is coupled with an end of the respective leg. With reference to FIG. 6D, the other end of each of the legs of arms 306B and 302A is coupled with a longitudinal section 308, such that the legs are substantially perpendicular to a longitudinal axis (not shown) of longitudinal section 308, and the compression link of each of arms 306B and 302A, is substantially parallel with this longitudinal axis. Similarly, the legs of arms 302B and 304A are coupled with a longitudinal section 310, and the legs of arms 304B and 306A are coupled with a longitudinal section 312.

Each of longitudinal sections 308, 310, and 312 imparts elasticity to the respective pair of arms. This elasticity forces for example, arms 306B and 302A, to move away from one another. Each of arms 302A, 302B, 304A, 304B, 306A, and 306B, and longitudinal sections 308, 310, and 312 is made of a biocompatible material, such as Titanium, and the like, or a shape memory alloy, such as Nitinol, and the like. Longitudinal sections 308, 310, and 312 are coupled together for example, by soldering, welding, an adhesive, and the like, in the configuration of the letter "Y". With reference to FIG. 6A, the physician inserts device 300 into the urethra, in a folded configuration (i.e., arms 302A and 306B close to one another, arms 302B and 304A close to one another, and arms 304B and 306A close to one another). Device 300 can be kept in the folded configuration for example, by tying together the respective pair of the compression links of arms 302A, 302B, 304A, 304B, 306A, and 306B, by a string (not shown). In this case, the actuating mechanism is made of elastic materials, and is configured to have a minimal energy state, when in the open configuration. Alternatively, in case of a shape memory alloy, device 300 can be maintained at a predetermined temperature to keep device 300 in the folded configuration (i.e., the force is produced due to a difference between thermal energies).

With reference to FIG. 6B, the physician moves device 300 to an open configuration, for example by subjecting device 300 to a predetermined temperature (i.e., in case of a shape memory alloy). Reverting to this open configuration causes arm 302A to move toward arm 302B, arm 304A to move toward arm 304B, and arm 306A to move toward arm 306B. The compression links of each of arms 302A, 302B, 304A, 304B, 306A, and 306B gradually pinch the respective tissue of the urethra and the prostate, thereby inducing ischemia in these tissues. With reference to FIG. 6D, in a final stage, the compression links of arms 302A and 302B isolate a tissue 314, the compression links of arms 304A and 304B isolate a tissue 316, and the compression links of arms 306A and 306B isolate a tissue 318. Tissues 314, 316, and 318 eventually dry out and are expelled from the body of the patient by the urine stream.

Figure 7B:
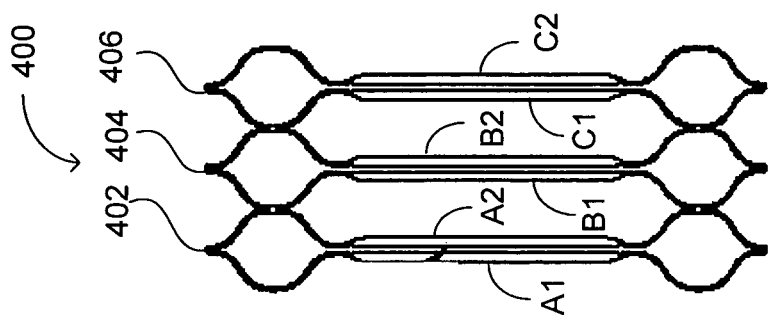
FIG. 7B is a schematic illustration of a top view of the device of FIG. 7A, in an operational configuration.
Figure 7A:
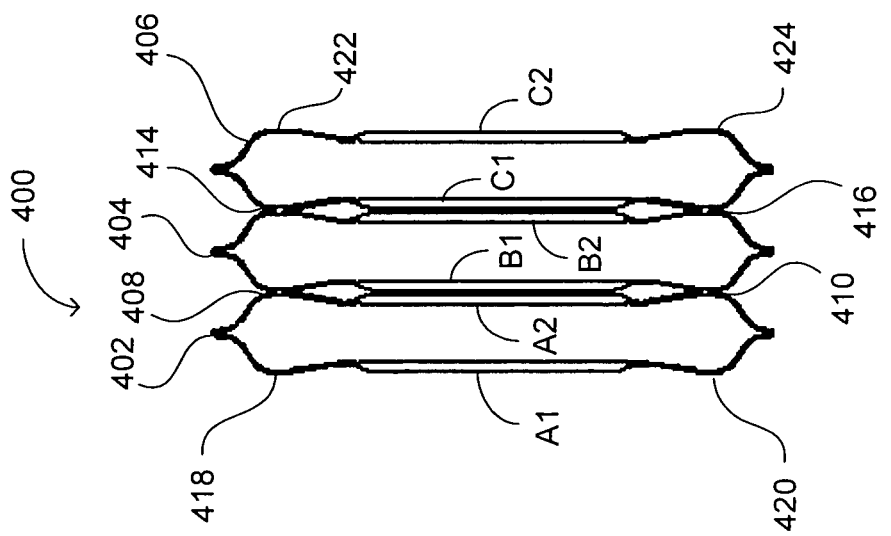
FIG. 7A is a schematic illustration of a top view of a device for dilating a urethra of the body of a patient, constructed and operative in accordance with another embodiment of the disclosed technique, in a pre-operational configuration.
Figure 8:
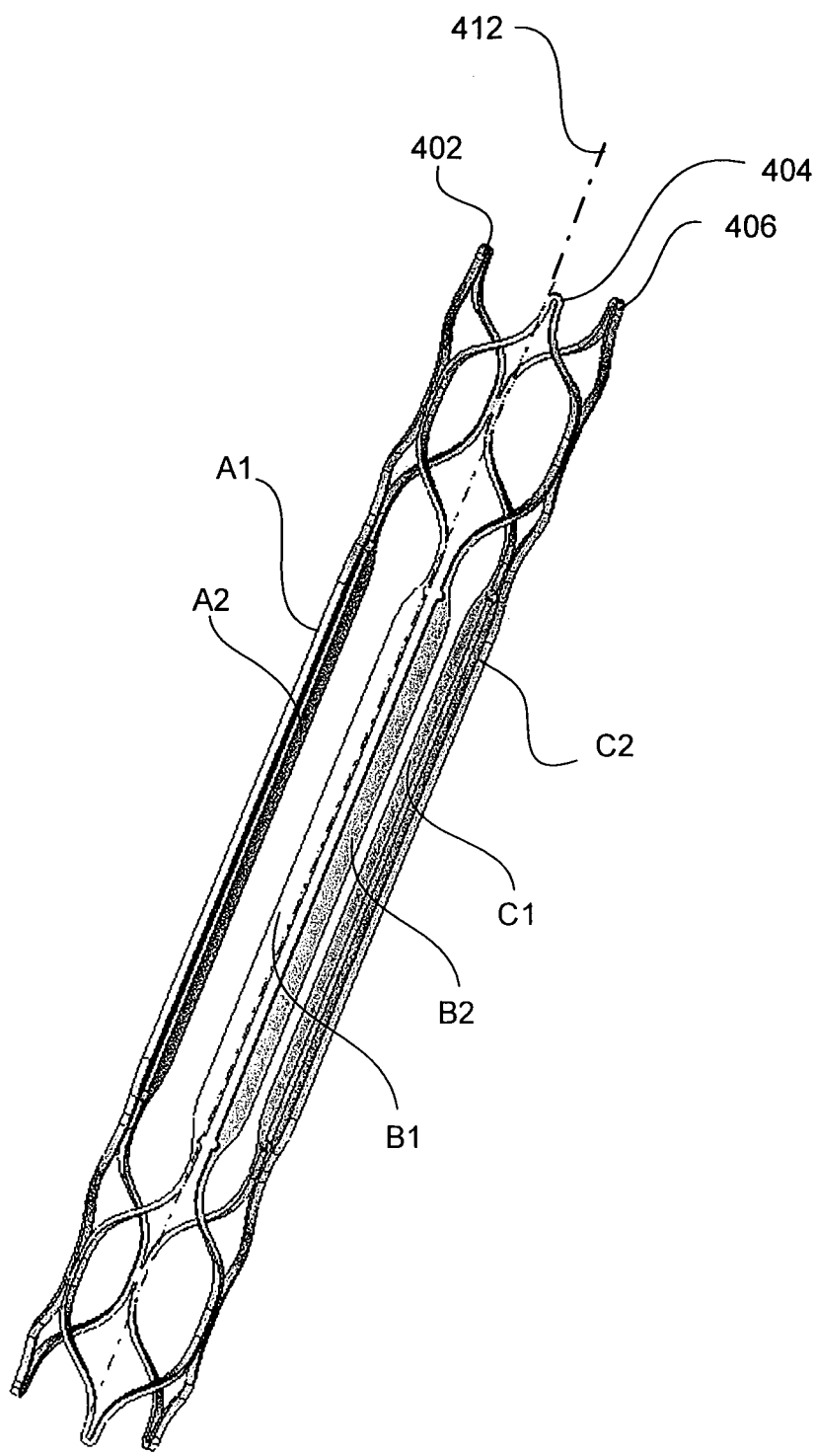
FIG. 8 is a schematic illustration in perspective, of the device of FIG. 7B, in an operational configuration, external to the urethra.
Figures 10, 11:
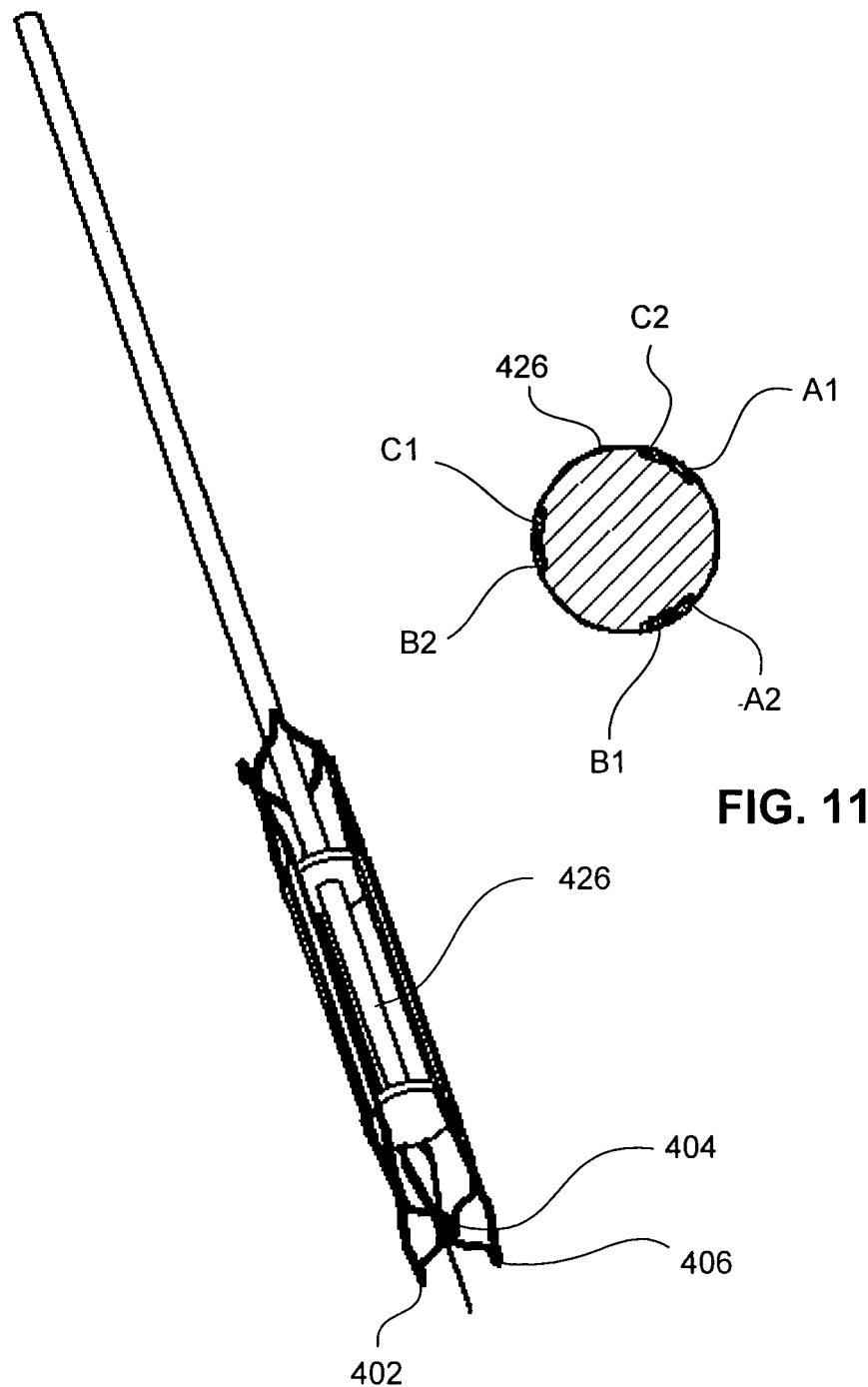
FIG. 10 is a schematic illustration in perspective, of the device of FIG. 7A, maintained in the pre-operational configuration by employing a keeper.
FIG. 11 is a schematic illustration of a cross section of the device of FIG. 10, together with the keeper.

Reference is now made to FIGS. 7A, 7B, 8, 9, 10, and 11. FIG. 7A is a schematic illustration of a top view of a device for dilating a urethra of the body of a patient, generally referenced 400, constructed and operative in accordance with another embodiment of the disclosed technique, in a pre-operational configuration. FIG. 7B is a schematic illustration of a top view of the device of FIG. 7A, in an operational configuration. FIG. 8 is a schematic illustration in perspective, of the device of FIG. 7B, in an operational configuration, external to the urethra. FIG. 9 is a schematic illustration in perspective, of the device of FIG. 8, in an operational configuration, within the urethra. FIG. 10 is a schematic illustration in perspective, of the device of FIG. 7A, maintained in the pre-operational configuration by employing a keeper. FIG. 11 is a schematic illustration of a cross section of the device of FIG. 10, together with the keeper.

With reference to FIG. 7A, device 400 includes a plurality of elongated closed-loop wires 402, 404, and 406. Closed-loop wire 402 includes compression sections A1 and A2. Closed-loop wire 404 includes compression sections B1 and B2. Closed-loop wire 406 includes compression sections C1 and C2. Closed-loop wires 402 and 404 are coupled together at points 408 and 410, along a longitudinal axis 412 (FIG. 8), of device 400. Closed-loop wires 404 and 406 are coupled together at points 414 and 416, along longitudinal axis 412. Closed-loop wires 402 and 406 are coupled together at points 418 and 420, along longitudinal axis 412, located on closed-loop wire 402, and at points 422 and 424, located on closed-loop wire 406. In this manner, closed loop wires 402, 404, and 406 form a closed loop assembly of rotatable arms. In order to clarify the construction of device 400, device 400 is illustrated in FIGS. 7A and 7B, in a configuration which corresponds to a stage before joining closed-loop wires 402 and 406, at points 418 and 420, and at points 422 and 424.

Each of closed-loop wires 402, 404, and 406 is made of a biocompatible elastic material (e.g., stainless steel or Nitinol), and the like, or a shape memory alloy (e.g., Nitinol). The physician inserts device 400 into the urethra, when device 400 is in the pre-operational configuration of FIG. 7A. Once the physician ensures that device 400 is located at the desired region within the urethra, the physician moves device 400 from the pre-operational configuration (FIG. 7A), to the operational configuration (FIG. 7B). For example, in case device 400 is made of an elastic material, the physician inserts device 400 into the urethra, when device 400 is maintained in the pre-operational configuration by employing a keeper 426 (FIG. 11). The physician inserts device 400 into the urethra, with keeper 426 located within device 400 (i.e., within the closed loop assembly of rotatable arms), thereby maintaining device 400 in the pre-operational configuration, as illustrated in FIG. 7A. In order to revert to the operational configuration, the physician pulls out keeper 426 from device 400, whereby the elastic force in closed-loop wires 402, 404, and 406 is released, forcing device 400 to the operational configuration as illustrated in FIG. 7B.

The elastic forces move compression sections A1 and A2 toward one another, compression sections B1 and B2 toward one another, and compression sections C1 and C2 toward one another. In this manner, each pair of compression sections A1 and A2, B1 and B2, and C1 and C2, pinch the respective regions of the urethra and the prostate of the body of the patient.

According to another aspect of the disclosed technique, the arms of a device similar to device 100 (FIG. 4A), pinch and incise the tissue of the prostate, instead of causing necrosis of the tissue by only pinching the tissue. When the incised tissue has dried up, a sheath is inserted into the urethra, over the dry tissue, over the over-tube, and the arms, and the tissue is removed from the urethra, thereby completing the procedure.

Incision of the tissue can be performed according to a method known in the art. For example, each of the arms can be in the form of a cutting blade having a sharp edge. When each pair of the arms approach one another, the cutting edges of each pair of the arms, approach one another over the tissue, and shear the tissue. Alternatively, the arms can be heated to a temperature sufficient for separating a desired portion of the tissue from the rest of the tissue. Heat may also be applied to the severed tissue, to induce coagulation of blood and stop the bleeding from the severed tissue. Further alternatively, the arms can be cooled to a temperature sufficient for separating the desired portion form the rest of the tissue. In case of heating, the electrical resistance of each of the arms is of such a value, that when an electrical potential is applied across the arm, the temperature of the arm rises. Alternatively, the arms can be in the form of a tube, whereby flow of a warm fluid within the tube, raises the temperature of the arm. In case of cooling, each of the arms can be in the form of a tube, whereby flow of a cryogenic fluid within the tube, lowers the temperature of the arm.

It is noted that by employing the device according to this aspect of the disclosed technique, the unnecessary tissue is cut instead of being pinched by device 100 (FIG. 3). In this case, much less time is necessary for the tissue to dry up and dislodge from the rest of the prostate tissue. Therefore, by employing the device according to this aspect of the disclosed technique, the physician can complete the operation much faster than by employing device 100.

According to a further aspect of the disclosed technique, each pair of the arms is made of two arcuate metal wires, which are fastened together at a longitudinal section thereof. The attachment at the longitudinal section imparts elasticity to the pair of arms, which forces the two arcuate metal wires towards one another. A delivery device inserts the arms into the urethra, while keeping the arms in the open configuration (i.e., keeping the two arcuate metal wires apart). When the physician ensures that the arms are located at the desired region of the prostate tissue, the physician releases a mechanism of the delivery device, to allow the two arcuate metal wires to approach one another, and pinch the enlarged prostate tissue.

The physician disengages the delivery device from the arms, and leaves the arms within the urethra, in the pinching state. The physician removes the arms from the urethra, together with the dead tissue of the enlarged portion of the prostate tissue, by pulling a string which is attached to a proximal end of the arms. For reducing the probability of injuring the urethra, the a sheath can be placed over the arms and dead tissue, before moving the device axially. Additionally, the device can include a tube, substantially parallel to the longitudinal section of the arms, and in the vicinity thereto, to keep the urethra open while the arms are forced on the enlarged tissue, and allow urine to flow from the bladder out of the body, through the urethra. The device can be placed between the bladder and the proximal sphincter, thus keeping the proximal sphincter operational, thereby enabling the patient control over his urine. Alternatively, the arms can be made of a shape memory alloy, to control the motion of the arms, by changing the temperature of the arms.

Figures 12, 13:
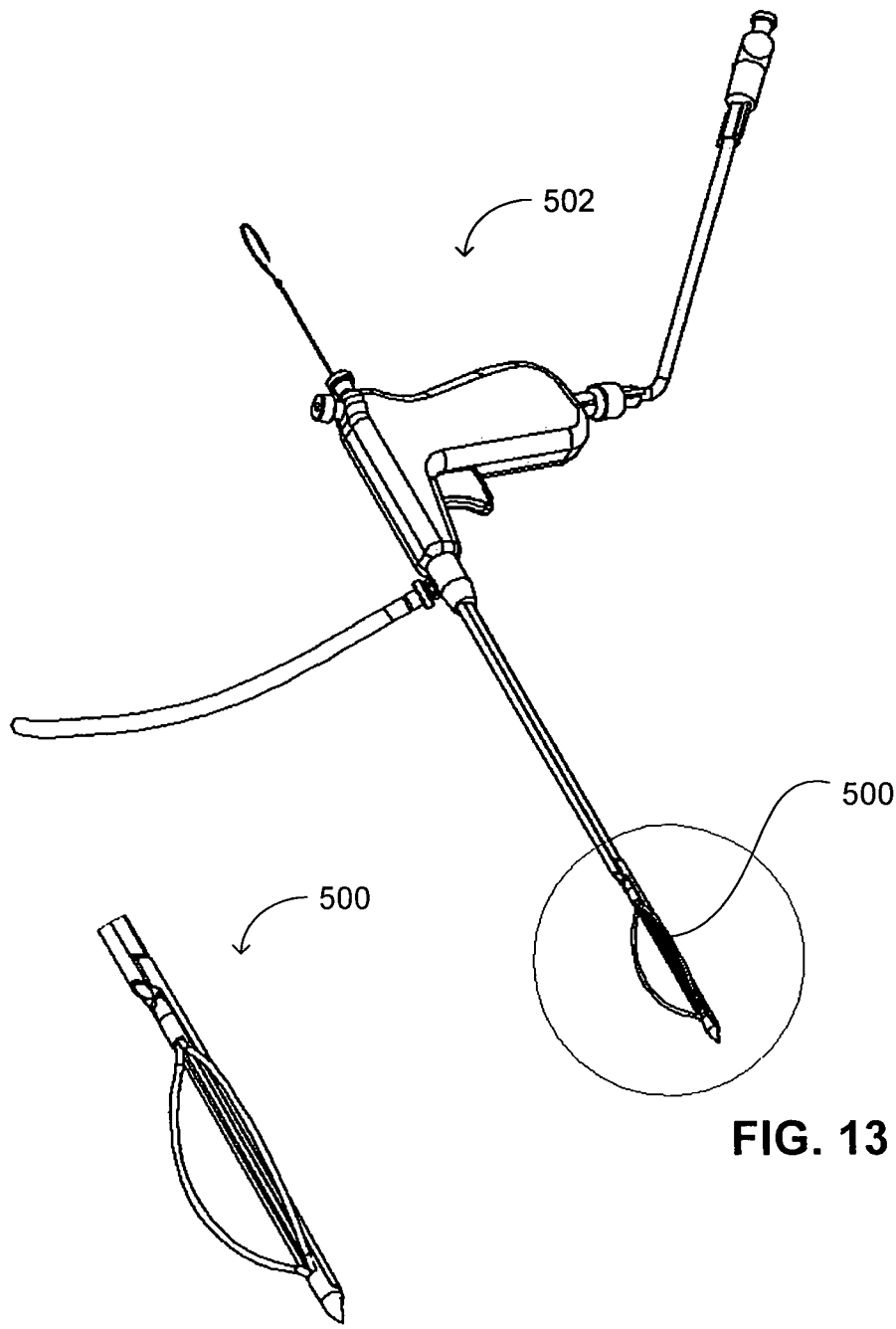
FIG. 12 is a schematic illustration in perspective, of a device, constructed and operative according to a further embodiment of the disclosed technique, in the open configuration.
FIG. 13 is a schematic illustration in perspective, of a delivery device.
Figure 14:
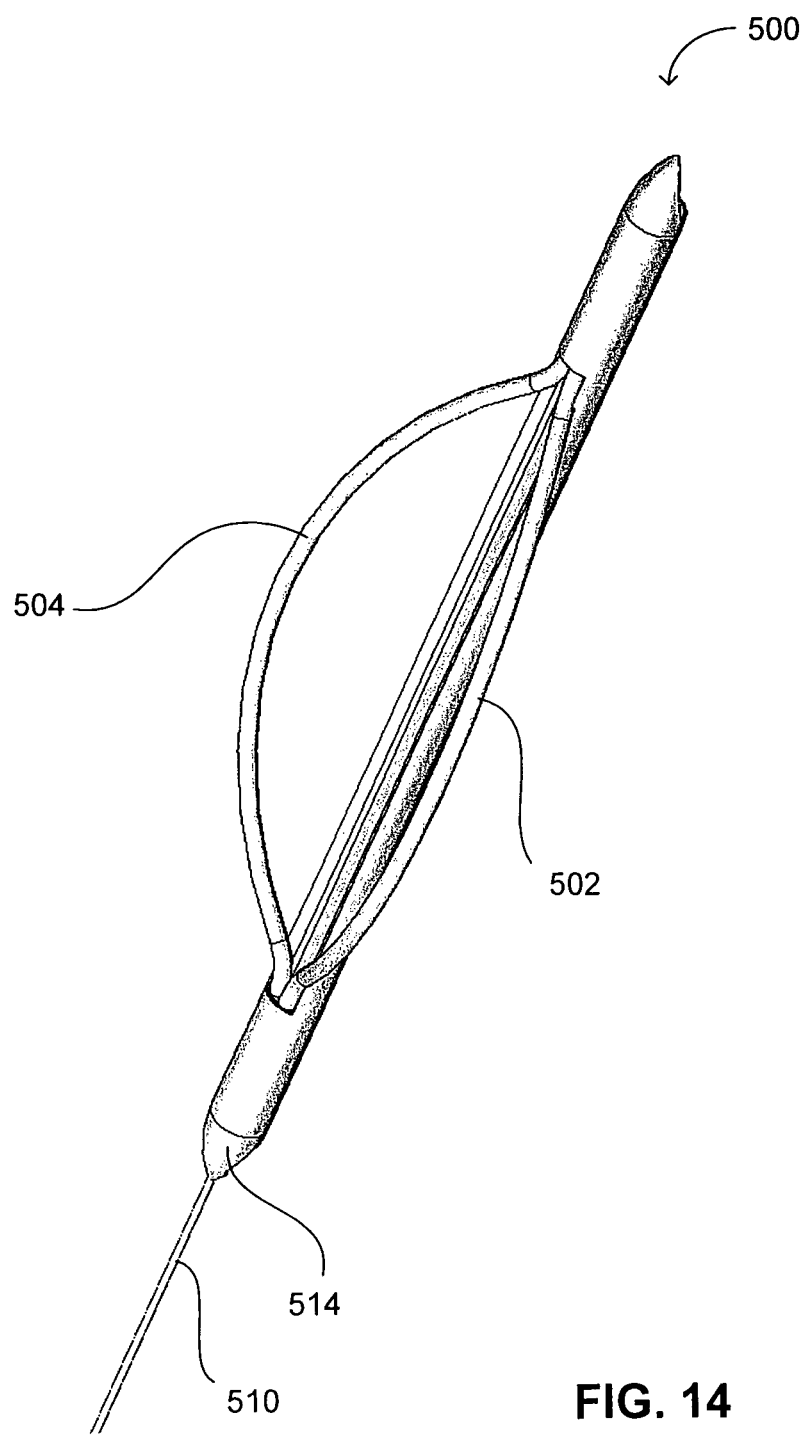
FIG. 14 is a schematic illustration in perspective, of the device of FIG. 12, in the open configuration.

Reference is now made to FIGS. 12, 13, 14, 15A, 15B, 16A, 16B, 17A, 17B, and 17C. FIG. 12 is a schematic illustration in perspective, of a device, generally referenced 500, constructed and operative according to a further embodiment of the disclosed technique, in the open configuration. FIG. 13 is a schematic illustration in perspective, of a delivery device, generally referenced 502. FIG. 14 is a schematic illustration in perspective, of the device of FIG. 12, in the open configuration. FIG. 15A is a schematic illustration in perspective, of the device of FIG. 12, in the open configuration. FIG. 15B is a schematic illustration in perspective, of the device of FIG. 12, in the closed configuration. FIG. 16A is a schematic illustration of a side view of the device of FIG. 15A. FIG. 16B is a schematic illustration of a side view of the device of FIG. 15B. FIG. 17A is a schematic illustration of a side view of the device of FIG. 15B. FIG. 17B is a schematic illustration of a top view of the device of FIG. 15B. FIG. 17C is a schematic illustration of a cross section of the device of FIG. 17B.

Device 500 includes a plurality (e.g., two) of arcuate metal wires 504 and 506, a tube 514, and a string 510. Arcuate metal wires 504 and 506 are fastened together for by welding, brazing, soldering, and the like, at a longitudinal region 512. String 510 is coupled with a proximal end 514 of device 500. Longitudinal region 512 imparts elasticity to arcuate metal wires 504 and 506, which tends to move arcuate metal wires 504 and 506 toward one another. The physician sets delivery device 502 in a delivery state, such that delivery device 502 keeps arcuate metal wires 504 and 506 in an open configuration, away from one another. When the physician ensures that device 500 is located at the enlarged portion of the tissue of the prostate, the physician employs delivery device 502, to release device 500, and allow the elastic force between arcuate metal wires 504 and 506, to move arcuate metal wires 504 and 506, to a closed configuration, toward one another, thereby pinching on the enlarged tissue. The physician disengages delivery device 502 from device 500, thereby leaving device 500 in the enlarged region of the urethra. The physician removes device 500 from the urethra, at a later time, by pulling on string 510, thereby removing the necrotic dry tissue of the enlarged portion of the prostate. When device 500 resides within the urethra, tube 514 keeps the lumen within the urethra open, in order to allow to the urine to flow.

Alternatively, arcuate metal wires 504 and 506 are made of a shape memory alloy. In this case, delivery device 502 maintains arcuate metal wires 504 and 506 in a martensite state, while device 500 is being delivered to the enlarged region of the prostate, and delivery device 502 transforms device 500 to an austenite state, when the physician ensures that device 500 is located at the enlarged region.

Figure 18:
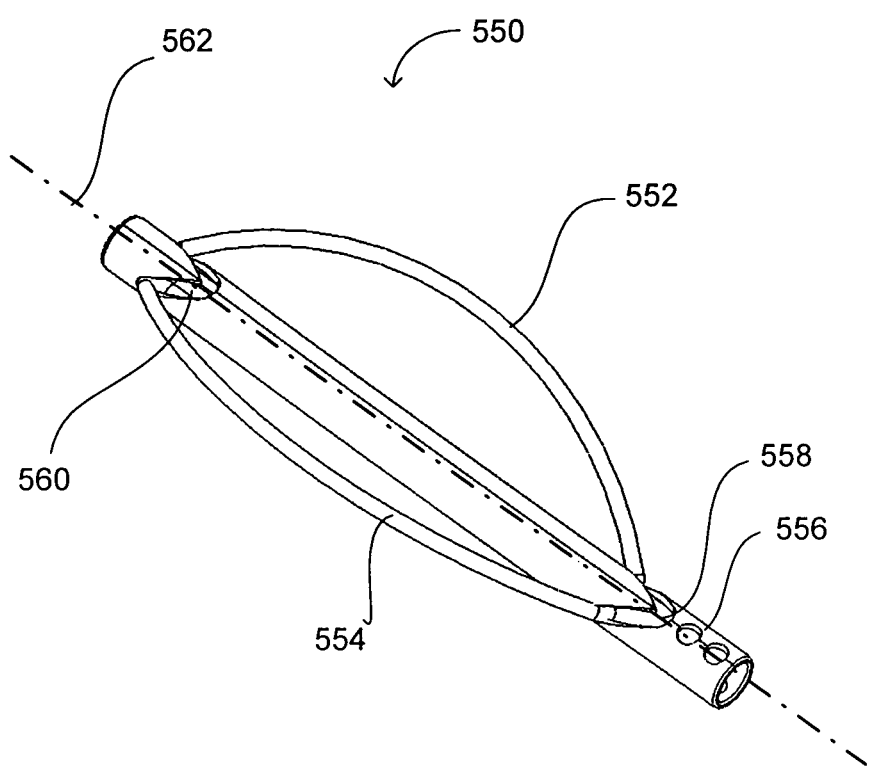
FIG. 18 is a schematic illustration in perspective, of a device constructed and operative according to another embodiment of the disclosed technique.

Reference is now made to FIG. 18, which is a schematic illustration in perspective, of a device generally referenced 550, constructed and operative according to another embodiment of the disclosed technique. Device 550 includes a pair of arcuate metal wires 552 and 554, and a rod 556. Rod 556 includes a first notch 558 and a second notch 560. A first end (not shown) and a second end (not shown) of arcuate metal wires 552 and 554, respectively, are coupled together. The first end and second end are substantially located along a longitudinal axis 562. Arcuate metal wires 552 and 554 can elastically rotate about longitudinal axis 562, on the two ends.

Each of first notch 558 and second notch 560 is slanted relative to longitudinal axis 562. The first end is located within first notch 558, and the second end is located within second notch 560. In the open configuration, the elastic force in between arcuate metal wires 552 and 554, tends to move the first end and the second end, away from one another. A delivery device (not shown) similar to device 502 (FIG. 13), maintains arcuate metal wires 552 and 554 in the open configuration. In order to move device 550 toward the closed configuration, the physician actuates the delivery device, to apply a force on the first end, toward the second end, against the elastic force between arcuate metal wires 552 and 554. Due to the oblique form of each of first notch 558 and of second notch 558, arcuate metal wires 552 and 554 approach one another, and device 550 moves toward the closed configuration.

Figure 19A:
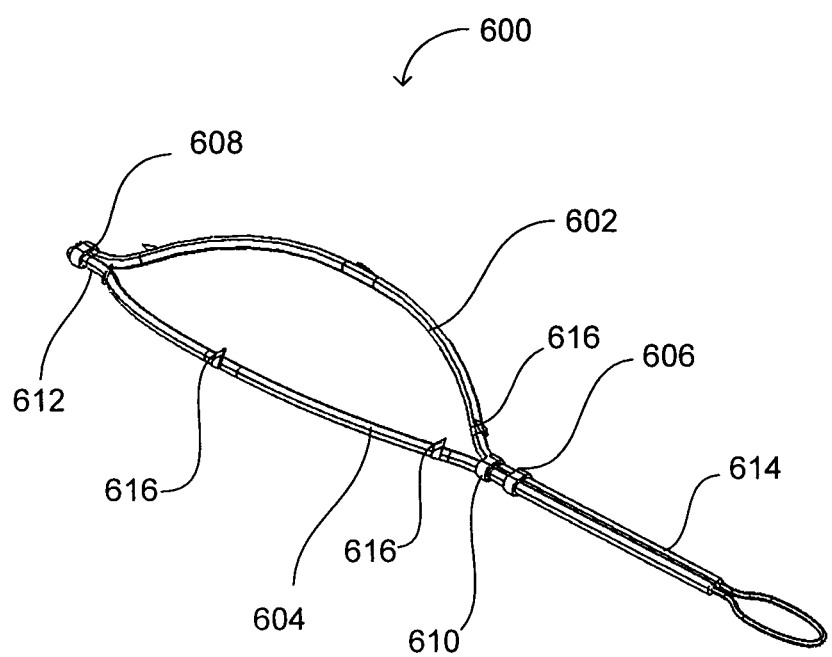
FIG. 19A is a schematic illustration in perspective, of a device constructed and operative according to a further embodiment of the disclosed technique, in an open configuration.
Figure 19B:
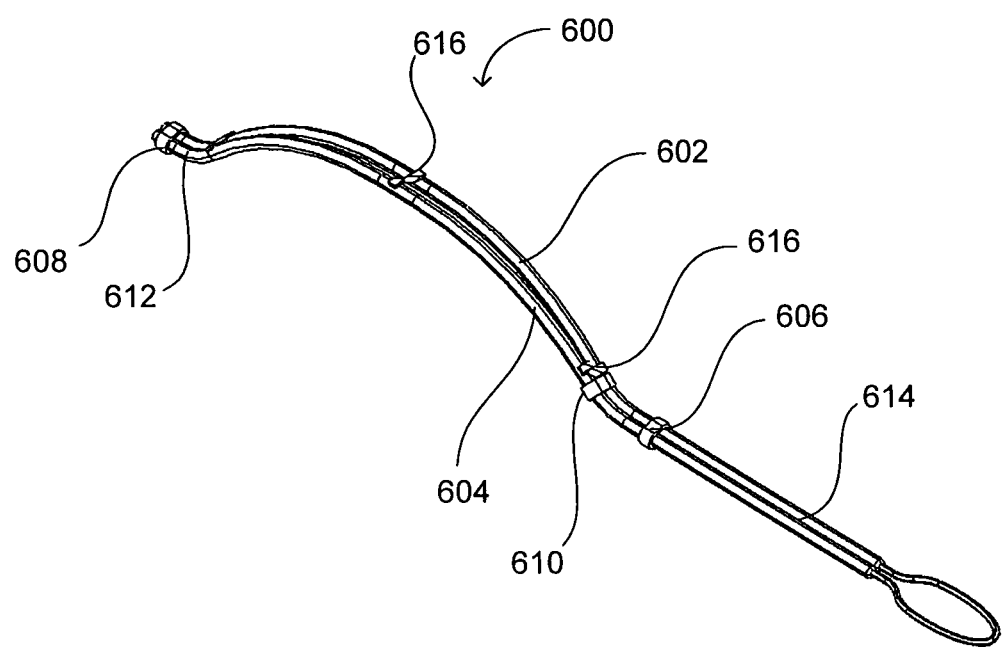
FIG. 19B is a schematic illustration in perspective of the device of FIG. 19A, in an closed configuration.

Reference is now made to FIGS. 19A and 19B. FIG. 19A is a schematic illustration in perspective, of a device generally referenced 600, constructed and operative according to a further embodiment of the disclosed technique, in an open configuration. FIG. 19B is a schematic illustration in perspective of the device of FIG. 19A, in an open configuration.

Device 600 includes a pair of wires 602 and 604, a rear fixed keeper 606, a front fixed keeper 608, and a sliding keeper 610. Device 600 includes a distal end 612, a proximal end 614, and a plurality of barbs 616. A length of distal end 612 is much shorter than a length of proximal end 614. Proximal end 614 is elongated, in order to attach device 600 to a delivery device similar to delivery device 502 (FIG. 13). Rear fixed keeper 606 is located at proximal end 614. Front fixed keeper 608 is located at distal end 612. Rear fixed keeper 606 and front fixed keeper 608 maintain wires 602 and 604, at distal end 612 and proximal end 614, respectively, coupled together. Each of rear fixed keeper 606 and front fixed keeper 608 is stationary relative to wires 602 and 604. Sliding keeper 610 is located at proximal end 614, between rear fixed keeper 606 and front fixed keeper 608. Sliding keeper 610 encloses wires 602 and 604, and can slide along wires 602 and 604. The sliding motion of sliding keeper 610, from proximal end 614 toward distal end 612, moves wires 602 and 604 towards one another (i.e., to a closed configuration), and sliding motion of sliding keeper 610, from distal end 612 toward proximal end 614, moves wires 602 and 604 apart (i.e., to an open configuration).

The physician inserts device 600 into the urethra, while device 600 is in the open configuration. When the physician ensures that device 600 is located at the enlarged region, the physician pushes sliding keeper 610 from proximal end 614 toward distal end 612, thereby moving device 600 to the closed configuration. Barbs 616 aid the physician to locate device 600 at a desired location along the enlarged portion of the prostate tissue. In addition, front fixed keeper 608 can be added or replaced with a front movable keeper, which is operative to move backward to further enforce wires 602 and 604 together.

It will be appreciated by persons skilled in the art that the disclosed technique is not limited to what has been particularly shown and described hereinabove. Rather the scope of the disclosed technique is defined only by the claims, which follow.

The invention claimed is:

1. An implantable device for removing prostate tissue from within the urethra, the implantable device is delivered by a delivery system into the urethra, when positioned within the urethra the implantable device disengages from the delivery system, the implantable device comprising:
  a plurality of arms, partially rotatable about a longitudinal axis of the urethra, said arms being divided into pairs of paired arms, each of said paired arms of each of said pairs being apart from each other in a first configuration and being adjoined against each other such that they restrict further rotation of each other, in a second configuration; and
  an actuating mechanism coupled to said arms,
  wherein said device is inserted in the urethra toward said prostate, in said first configuration and
  wherein after said device is placed adjacent to said prostate, within said urethra, said actuating mechanism moves each of said paired arms of each of said pairs toward each other until each of said paired arms adjoin each other and restrict further rotational movement of each other, thereby each of said pairs pinches said prostate through said urethra for inducing ischemia and necrosis in the pinched tissues.

2. The device according to claim 1, wherein each of said rotatable arms is in the form of a non-cutting device, having a blunt edge, and wherein rotatable arms of said second configuration apply a compression force on an enlarged portion of said prostate, to prevent blood flow to said enlarged portion.

3. The device according to claim 1, wherein each of said plurality of arms partially rotates about said longitudinal axis, without completing a full rotation about said longitudinal axis.

* * * * *

UNITED STATES PATENT AND TRADEMARK OFFICE
CERTIFICATE OF CORRECTION

PATENT NO. : 8,603,187 B2
APPLICATION NO. : 12/598996
DATED : December 10, 2013
INVENTOR(S) : Kilemnick et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 616 days.

Signed and Sealed this
Twenty-second Day of September, 2015

Michelle K. Lee
*Director of the United States Patent and Trademark Office*